(12) United States Patent
Overweg et al.

(10) Patent No.: US 10,324,148 B2
(45) Date of Patent: Jun. 18, 2019

(54) ACTIVE COMPENSATION FOR FIELD DISTORTING COMPONENTS IN A MAGNETIC RESONANCE IMAGING SYSTEM WITH A GANTRY

(71) Applicant: KONINKLIJKE PHILIPS N.V., Eindhoven (NL)

(72) Inventors: Johannes Adrianus Overweg, Eindhoven (NL); Falk Uhlemann, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 947 days.

(21) Appl. No.: 14/763,525

(22) PCT Filed: Jan. 16, 2014

(86) PCT No.: PCT/EP2014/050743
§ 371 (c)(1),
(2) Date: Jul. 27, 2015

(87) PCT Pub. No.: WO2014/121991
PCT Pub. Date: Aug. 14, 2014

(65) Prior Publication Data
US 2016/0011288 A1 Jan. 14, 2016

(30) Foreign Application Priority Data
Feb. 6, 2013 (EP) .................................... 13154203

(51) Int. Cl.
*G01R 33/48* (2006.01)
*G01R 33/3875* (2006.01)
*G01R 33/389* (2006.01)
*A61B 5/055* (2006.01)
*A61N 5/10* (2006.01)
(Continued)

(52) U.S. Cl.
CPC ........ *G01R 33/4808* (2013.01); *A61B 5/0555* (2013.01); *A61N 5/1039* (2013.01);
(Continued)

(58) Field of Classification Search
CPC .............. G01R 33/4808; G01R 33/307; G01R 33/3875; G01R 33/389; G01R 33/56383; A61B 5/0555; A61N 5/1039
(Continued)

(56) References Cited

U.S. PATENT DOCUMENTS 7,663,368 B2 2/2010 Lazar et al.
8,482,282 B2 7/2013 Fautz
(Continued)

FOREIGN PATENT DOCUMENTS

WO 2005069032 A1 7/2005
WO 2010076676 A1 7/2010
(Continued)

OTHER PUBLICATIONS

Wachowicz et al, "Geometric Distortion and Shimming Considerations.." Medical Physics, AIP, vol. 39, No. 5, May 1, 2012 p. 26599-2668.
(Continued)

*Primary Examiner* — Jeff W Natalini
*Assistant Examiner* — Steven L Yeninas

(57) ABSTRACT

A medical apparatus (300, 400, 500) includes a magnetic resonance imaging system (306); magnetic compensation coils (334, 335) for compensating for magnetic inhomogeneities within the imaging zone; a gantry (308) operable for rotating about the imaging zone; a position sensor (312) for measuring the angular position and the angular velocity of the gantry; at least one magnetic field distorting component (310, 510, 512) in the gantry; and a memory (362) storing machine executable instructions (380, 382, 410, 530, 532) and field correction data (372). The instructions cause a processor to: receive (100, 200) the position and angular velocity data from the position sensor; determine (102, 202) coil control commands (374) for controlling the magnetic compensation coils using the field correction data, the posi-
(Continued)

tion data and the angular velocity data; control (104, 204) the magnetic compensation coils to compensate for magnetic inhomogeneities within the imaging zone using the coil control commands; and acquire (106, 212) the magnetic resonance data.

20 Claims, 6 Drawing Sheets

(51) Int. Cl.
  *G01R 33/30* (2006.01)
  *G01R 33/563* (2006.01)
  *G01R 33/565* (2006.01)
(52) U.S. Cl.
  CPC ......... *G01R 33/307* (2013.01); *G01R 33/389* (2013.01); *G01R 33/3875* (2013.01); *G01R 33/56383* (2013.01); *A61N 2005/1055* (2013.01); *G01R 33/4812* (2013.01); *G01R 33/56563* (2013.01)
(58) Field of Classification Search
  USPC ................ 324/300–322; 382/128–131; 600/407–435
  See application file for complete search history.

(56) References Cited

U.S. PATENT DOCUMENTS

| 2001/0001807 | A1* | 5/2001 | Green | A61N 5/1042 600/411 |
| 2010/0087730 | A1* | 4/2010 | Yamada | A61B 5/055 600/419 |
| 2011/0012593 | A1 | 1/2011 | Shvartsman et al. | |
| 2011/0112351 | A1* | 5/2011 | Fordyce, II | A61N 5/103 600/1 |

FOREIGN PATENT DOCUMENTS

| WO | 2012063158 A1 | 5/2012 | |
| WO | 2012164527 A1 | 12/2012 | |
| WO | WO 2012164527 A1 * | 12/2012 | ......... G01R 33/4808 |

OTHER PUBLICATIONS

El-Sharkawy et al "Monitoring and Correcting Spatio-Temporal Variations.." Magnetic Resonace Materials in Physics Biology and Medicine, vol. 19, No. 5 Oct. 17, 2006, p. 223-236.

* cited by examiner

ACTIVE COMPENSATION FOR FIELD DISTORTING COMPONENTS IN A MAGNETIC RESONANCE IMAGING SYSTEM WITH A GANTRY

CROSS-REFERENCE TO PRIOR APPLICATIONS

This application is the U.S. National Phase application under 35 U.S.C. § 371 of International Application No. PCT/EP2014/050743, filed on Jan. 16, 2014, which claims the benefit of EP Patent Application No. EP13154203.7, filed on Feb. 6, 2013. These applications are hereby incorporated by reference herein.

TECHNICAL FIELD OF THE INVENTION

The invention relates to magnetic resonance imaging, in particular to magnetic resonance guided radiotherapy.

BACKGROUND OF THE INVENTION

Integration of Magnetic Resonance (MR) and Linear Accelerators (LINAC) or

Magnetic Resonance and other modalities of radiotherapy opens new horizons in Radiotherapy by improved lesion targeting, especially for moving organs. In a practical implementation proposal, the LINAC rotates around the patient to hit the gross target volume (GTV) and clinical target volume (CTV) from multiple angles while minimizing the radiation exposure for surrounding tissues. A difficulty is that as the radiation source is moved around the magnet, active and/or passive components of the radiotherapy system may cause magnetic field distortions.

An example of a magnetic resonance imaging system combined with a LINAC is described in WO 2012/063158 A1.

In El-Sharkawy et al., MAGMA. 2006 November; 19(5): 223-236, doi: 10.1007/s10334-006-0050-2 discusses the homogeneity and stability of the static magnetic field in magnetic resonance imaging. Serial field mapping and phased difference imaging correction is used to correct for spatial and temporal field drifting during phase sensitive MR protocols.

SUMMARY OF THE INVENTION

The invention provides for a medical apparatus, a method, and a computer program product in the independent claims. Embodiments are given in the dependent claims. As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a medical apparatus comprising a magnetic resonance imaging system for acquiring magnetic resonance data from an imaging zone. The magnetic resonance imaging system comprises a magnet operable for generating a magnetic field within the imaging zone. The medical apparatus further comprises magnetic compensation coils for compensating for magnetic inhomogeneities within the imaging zone. The magnetic compensation coils may take different forms in different embodiments. In some embodiments the magnetic compensation coils are the normal gradient coils used in the magnetic resonance imaging system. In some other embodiments the magnetic compensation coils may be separate coils from the gradient coils specifically for compensating for magnetic inhomogeneities. In particular they may compensate for higher order corrections than the gradient coils normally do. In some embodiments the magnetic compensation coils are a combination of the conventional gradient coils and additional coils used to compensate for higher order corrections to the magnetic field.

The medical apparatus further comprises a gantry may contain a medial apparatus such as an external beam radiation treatment system. The gantry is operable for rotating about the imaging zone. The gantry is configured to rotate about a rotational axis. In the case where the magnet is a cylindrical magnet the rotational axis of the gantry may be aligned with the axis of symmetry of the cylindrical magnet. In some other embodiments the rotational axis may have a position adjustable with respect to the axis of symmetry of the magnet. The medical apparatus further comprises a position sensor for measuring position data descriptive of an angular position of the gantry. In some embodiments the position sensor may also measure the angle of velocity of the gantry.

The medical apparatus installed on the rotating gantry further comprise at least one magnetic field distorting component. The magnetic field distorting component may be either an active or a passive component which may affect or change the magnetic field generated by the magnet. The gantry is further operable to rotate the at least one magnetic field distorting component about the rotational axis. In the case where the at least one magnetic field distorting component are not distributed symmetrically about the gantry when they are moved by the gantry they may cause the magnetic field within the imaging zone to change as a function of the position of the gantry. The medical apparatus further comprises a memory for storing machine-executable instructions and field correction data. The field correction data is descriptive of the magnetic field within the imaging zone as a function of at least the angular position. In some embodiments it may also be a function of the angular velocity and also the prior locations/configurations of the gantry.

The medical apparatus further comprises a processor for controlling the medical apparatus. Execution of the instructions causes the processor to receive the position data from the position sensor. Execution of the instructions further cause the processor to determine coil control commands for controlling the magnetic compensation coils using the field correction data and the position data. Controlling the coils is to be read as setting magnitude and direction of DC currents in the coils or applying DC offsets to already flowing currents so as to create the desired magnetic response. Execution of the instructions further cause the processor to control the magnetic compensation coils to compensate for magnetic inhomogeneities within the imaging zone caused by the at least one magnetic field distorting component using the coil control commands. Execution of the instructions further causes the processor to acquire the magnetic resonance data using the magnetic resonance imaging system.

Essentially as the gantry rotates the at least one magnetic field distorting component is moved and causes inhomogeneities of the magnetic field within the imaging zone. The field correction data may be data which is acquired previously and is used to either directly control or generate control commands which are used to control the magnetic compensation coils to compensate for these inhomogeneities which are introduced by the motion of the at least one magnetic field distorting component.

This arrangement may be particularly beneficial because the changes to the magnetic field within the imaging zone may be relatively complex with respect to the position of the gantry. This is because of the large magnetic field generated by the magnet. In addition to the magnet and any field which is generated actively or passively by the at least one magnetic field distorting component there are also other metal or magnetic objects within the vicinity that may couple to the motion of the at least one magnetic field distorting component. For instance if a magnetic resonance imaging system were installed in a building and there were metal or ferromagnetic bars within the concrete, these bars may generate a magnetic field after becoming magnetized. Without the presence of a gantry these permutations in the magnetic field would normally be compensated for by shimming the magnet. However, when the magnetic field distorting component is moving this may introduce changes in the magnetic field of the metal bars which then in turn also affects the magnetic field within an imaging zone. As a result there may be low frequency changes in the magnetic field within the imaging zone as the gantry is used. The system or medical apparatus described above may be capable of compensating for such complex changes in the magnetic field due to motion of the at least one magnetic field distorting component.

It should be noted that any of the methods or procedures described herein may be done repeatedly. This includes the previously described instructions which control the processor and also any instructions or methods after this statement.

In another embodiment the position sensor is further operable for measuring an angular velocity of the gantry. The position data is further descriptive of the angular velocity of the gantry. The field correction data is further descriptive of the magnetic field within the imaging zone as a function of angular position and the angular velocity. This embodiment may be particularly beneficial when there is a coupling between the magnetic field distorting component and the magnet via a third magnetic object such as the rebar in the concrete that was mentioned earlier. The effect on the magnetic field may be more complicated than a relationship which is purely related on the position of the magnetic field distorting component. The effect on the field within the imaging zone may also be dependent upon how rapidly the magnetic field distorting component is moving or its configuration (e.g. multi-leaf collimator). This embodiment may be able to compensate for such a relationship.

In another embodiment the field correction data is further descriptive of the magnetic field within the imaging zone as a function of prior angular position of the gantry. Execution of the instructions further causes the processor to log the position data in a position database and also to determine prior angular positions of the gantry from the position database. The coil control commands are determined using the field correction data, the position data and the prior angular positions. In some embodiments the angular velocity may also be used. This embodiment may be beneficial when the coupling of the magnetic field distorting component depends also where it was and not just on where it's present position is. This may be particularly beneficial when there is a hysteresis effect. In some embodiments the prior position, the current position and also the angular velocity may be important.

In another embodiment the field correction data comprises pre-calculated coil control commands. In this case depending upon what is stored in the position data the pre-calculated coil control commands may have values which can be used to drive control commands directly or may contain control commands which enable the processor to directly set the proper currents in the magnetic compensation coil to correct the homogeneity of the magnetic field.

In another embodiment the field correction data comprises spatially dependent magnet field measurements within the imaging zone. The coil control commands are determined using the magnetic field model of the magnetic compensation coils to compensate for spatially dependent magnetic field measurements. In this case the spatially dependent field perturbations which are caused by the motion or position of the at least one magnetic field distorting component are stored and these are then used to calculate the coil control commands. This embodiment may be beneficial when there are other effects which cause the magnetic field to vary also. In this way other changes in the magnetic field can be taken into account and then the proper correction to account for all inhomogeneities in the field can be performed.

In another embodiment execution of the instructions further cause the processor to measure magnetic field magnetic resonance data using the magnetic resonance imaging system before measuring the magnetic resonance data. Execution of the instructions further causes the processor to determine the magnetic field change within the imaging zone. The magnetic field magnetic resonance data as used herein encompasses magnetic resonance data that contains data which can be used for determining the relative and/or absolute value of the magnetic resonance field for the purpose of correcting the magnetic resonance field. For instance El-Sharkawy et. al. describes a serial field mapping technique.

In another embodiment execution of the instructions further cause the processor to calculate a phase offset using the magnetic field change. Execution of the instructions further cause the processor to correct the magnetic resonance data using the phase offset. In this case the inhomogeneities of the magnetic field may cause small variations in the phase measurement when magnetic resonance data is acquired. In the previously mentioned article by El-Sharkawy et. al, a technique is mentioned of serial field mapping and phase difference imaging correction that may be used for performing such a correction. This embodiment may be beneficial because the magnetic field is compensated for by using the magnetic compensation coils than any other remaining inhomogeneities are corrected by performing the correction using the phase offset.

In another embodiment execution of the instructions further causes the processor to modify the coil control commands to compensate for the magnetic field change.

In another embodiment the medical device comprises a radio therapy device. The radio therapy device comprises at least one magnetic field distorting component. This may be a very typical embodiment because radio therapy devices typically contained such things as electron or charged particle objects which may affect the magnetic field.

In another embodiment the radio therapy device is any one of the following: a Linac, a charged particle source, and an X-ray source.

In another embodiment the at least one magnetic field distorting component comprises: a magnetic field source, a coil, a solenoid, charged particle objects, a magnet, an electromagnet, a collimator for X-Rays, a transformer, a magnetron, a microwave circulator, an electric motor, an electric heater, an electric power distribution system, a relay, an electrically actuated valve, a permanent magnet, a ferromagnetic component, a magnetic component, and combinations thereof.

In another aspect the invention provides for a method of controlling the medical apparatus. The medical apparatus comprises a magnetic resonance imaging system for acquiring magnetic resonance data from an imaging zone. The magnetic resonance imaging system comprises a magnet for generating a magnetic field within the imaging zone. The medical apparatus further comprises magnetic compensation coils for compensating for magnetic inhomogeneities within the imaging zone. The medical apparatus further comprises a gantry operable for rotating about the imaging zone. The gantry is configured to rotate about a rotational axis. The medical apparatus further comprises a position sensor for measuring position data descriptive of an angular position of the gantry. The medical apparatus further comprises at least one magnetic field distorting component. The gantry is further operable to rotate the at least one ferromagnetic or electromagnetic field generating distorting component about the rotational axis.

The method comprises the step of receiving the position data from the position sensor. The method further comprises the step of determining coil control commands for controlling the magnitude and direction of the current flowing in the magnetic compensating coils using the field correction data and the position data. The field correction data is descriptive of the magnetic field within the imaging zone as a function of the angular position. The method further comprises controlling the magnetic compensation coils to compensate for magnetic inhomogeneities within the imaging zone caused by the at least one magnetic field distorting component. The method further comprises acquiring the magnetic resonance data using the magnetic resonance imaging system. The method may also include reconstructing the magnetic resonance image from the magnetic resonance data.

In another embodiment the position sensor is further operable for measuring the angular velocity of the gantry. The position data is further descriptive of the angular velocity of the gantry. The field correction data is further descriptive of the magnetic field within the imaging zone as a function of the angular position and the angular velocity.

In another embodiment the field correction data is further descriptive of the magnetic field within the imaging zone as a function of prior angular position of the gantry. The method further comprises the step of logging the position data in a position database. The method further comprises the step of determining prior angular positions of the gantry from the position database. The coil control commands are determined using the field correction data, the position data and the prior angular positions.

In another embodiment the method further comprises the step of measuring the magnetic field in the imaging zone. The magnetic field is measured using any one of the following: a magnetometer, a magnetic resonance protocol to control the magnetic resonance imaging system, and combinations thereof. The method further comprises the step of determining the field correction data using the magnetic field measurements.

In another aspect the invention provides for a computer program product for controlling the medical apparatus according to an embodiment of the invention. Execution of instructions contained within the computer program product cause the processor to control the medical apparatus such that the medical apparatus is controlled in accordance with any of the previously described embodiments.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
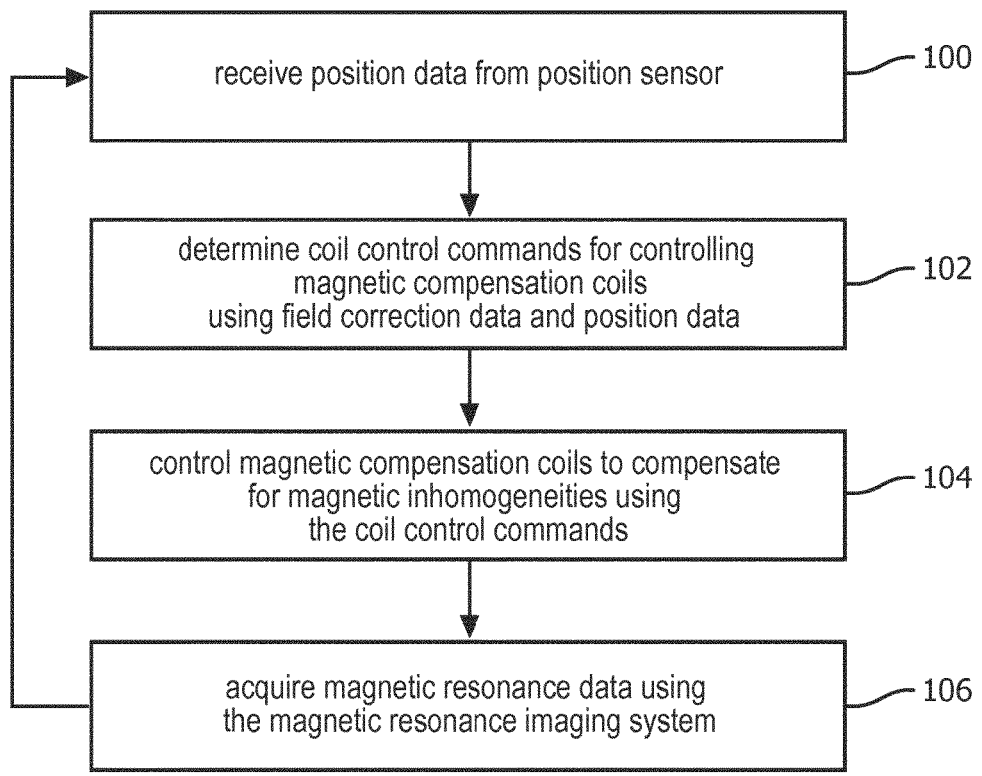
FIG. 1 shows a flow diagram which illustrates an example of a method.

FIG. 1 shows a flow diagram which illustrates an example of a method. First in step 100 position data is received from a position sensor. Next in step 102 coil control commands are determined for controlling magnetic compensation coils using field correction data and position data. Next in step 104 magnetic compensation coils are controlled to compensate for magnetic inhomogeneities using the coil control commands. Next in step 106 magnetic resonance data is acquired using the magnetic resonance imaging system. This method may be repeated in a loop until all of the magnetic resonance data is acquired. Thus, as the gantry is moving the changing inhomogeneities in the magnetic fields caused by the magnetic field distorting component may be continually compensated for.

Figure 2:
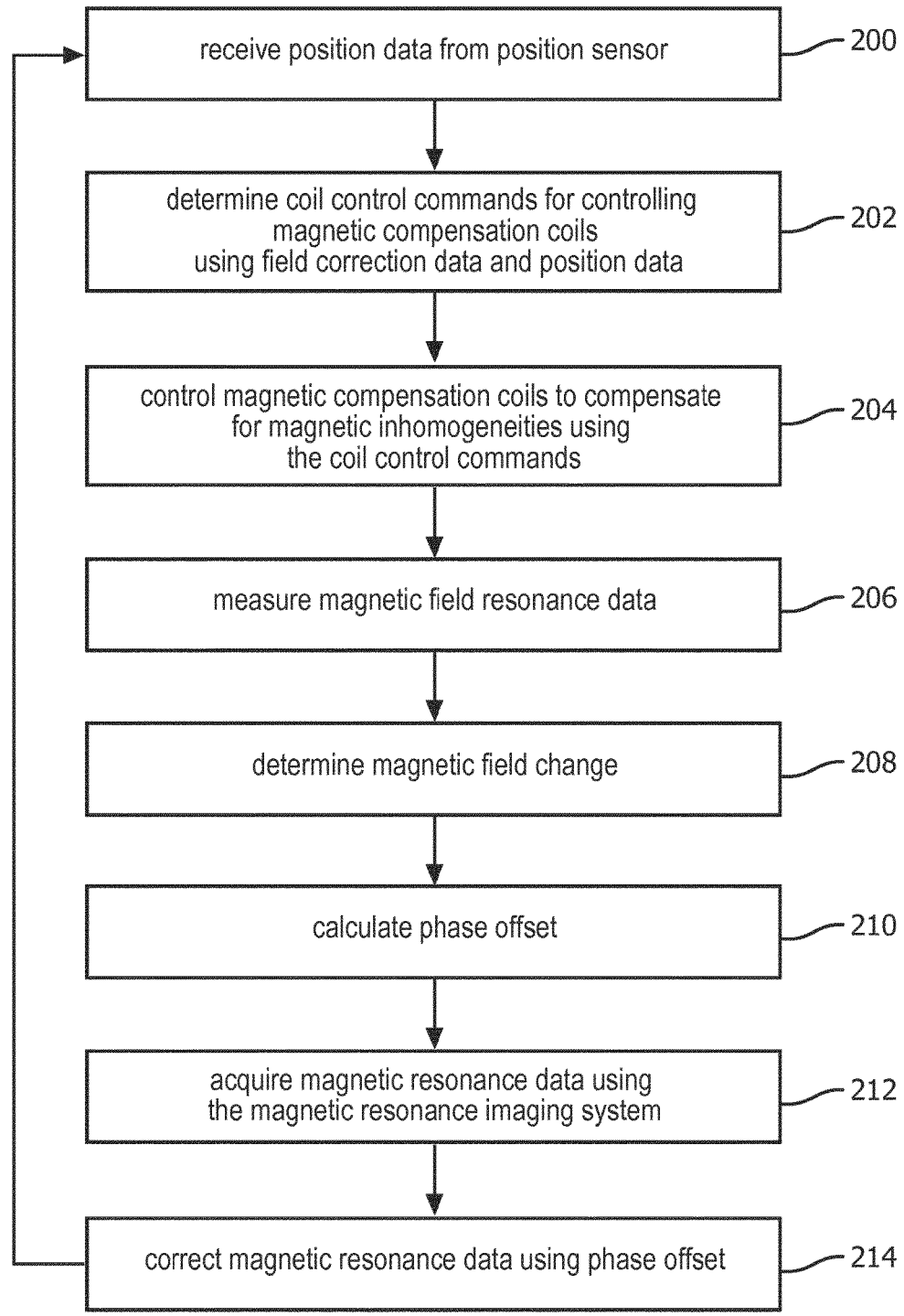
FIG. 2 shows a flow diagram which illustrates a further example of a method.

FIG. 2 shows a flow diagram which illustrates another example of the method. First in step 200 position data is received from the position sensor. Next in step 202 coil control commands are determined for controlling magnetic compensation coils using field correction data and position data. Next in step 204 magnetic compensation coils are controlled to compensate for magnetic inhomogeneities using the coil control commands. Next in step 206 magnetic field resonance data is measured. In step 208 the magnetic field changes are determined. In step 210 a phase offset is calculated. Next in step 212 magnetic resonance data is acquired using the magnetic resonance imaging system. And finally in step 214 the magnetic resonance data is corrected using the phase offset. In some embodiments this method may be repeated as a loop and the position data from the position sensor may be received in step 200 again. This may be repeated until all the magnetic resonance data is acquired.

Figure 3:
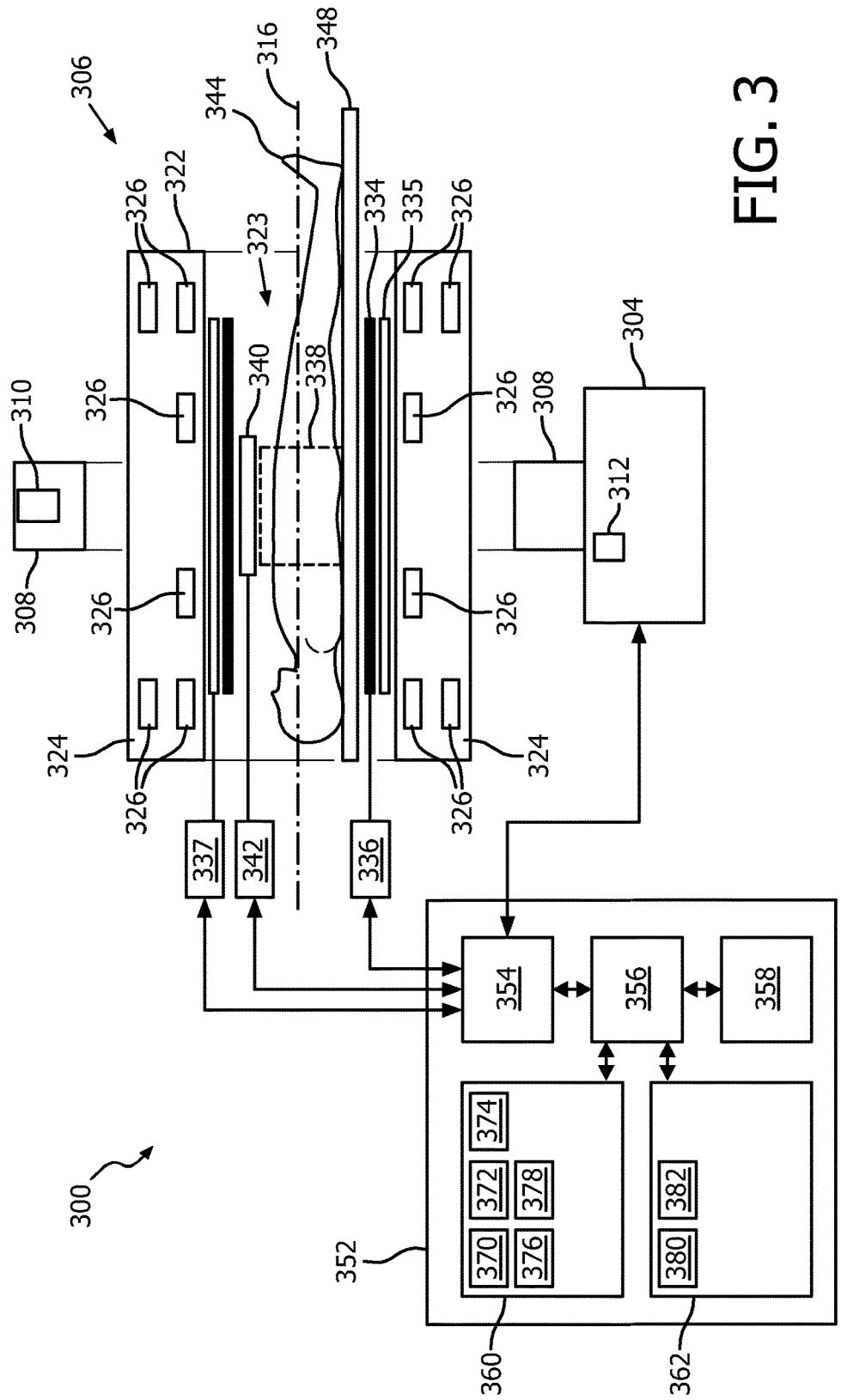
FIG. 3 illustrates an example of a medical instrument.

FIG. 3 shows a cross-sectional and functional view of a therapeutic apparatus 300 according to an embodiment of the invention. The therapeutic apparatus 300 is shown as comprising a gantry 308 with a mechanical actuator 104 and a magnetic resonance imaging system 306. The gantry 308 supports a magnetic field distorting component. The gantry 308 motion is controlled by the mechanical actuator 304. A position sensor within the mechanical actuator 312 is shown. The position sensor does not need to be within the mechanical actuator.

The position sensor 312 is capable of measuring at least the rotational position of the gantry 308. Within the gantry 308 there is a magnetic field distorting component 310.

The magnetic resonance imaging system 306 is shown as comprising a magnet 322. As the gantry 308 rotates the magnetic field distorting component 310 is also rotated. This may directly cause inhomogeneities in the magnetic field of the imaging zone 338 or it may react with the magnetic field of objects surrounding the medical apparatus 300 thereby indirectly causing changes in the magnetic field of a magnet 322 of the magnetic resonance imaging system 306.

The gantry 308 is ring-shaped and surrounds the magnet 322. The magnet 322 shown in FIG. 3 is a cylindrical type superconducting magnet. The magnet 332 has a bore 323 through the center of it. However, other magnets are also applicable for embodiments of the invention. The magnet 322 has a supercooled cryostat 324. Inside the cryostat 324 there is a collection of superconducting coils 326. The cylindrical magnet 322 is shown as sharing an axis 316 of symmetry with the rotational axis of the gantry. However the axis of symmetry and the rotational axis need not be coaxial.

Within the bore of the magnet there is a magnetic field gradient coil 334 which is used for acquisition of magnetic resonance data to spatially encode objects within an imaging zone 338 of the magnet 322. The magnetic field gradient coil 334 is connected to a magnetic field gradient coil power supply 336. The magnetic field gradient coil 334 is intended to be representative. Typically magnetic field gradient coils contain three separate sets of coils for spatially encoding in three orthogonal spatial directions. The imaging zone 338 is located in the centre of the magnet 322.

Adjacent to the magnetic field gradient coil 334 is shown a magnetic compensation coil 335. The magnetic compensation coils 335 in this embodiment are coils which are able to compensate for a higher order field inhomogeneities than the magnetic field gradient coil can. The magnetic compensation coil 335 is connected to a magnetic compensation coil power supply 337. In some embodiments the magnetic compensation coil 335 and the magnetic compensation coil power supply 337 are not present. In other embodiments the magnetic field gradient coil 334 and the magnetic compensation coil 335 are combined. Similarly, in some embodiments the magnetic field gradient coil power supply 336 and the magnetic compensation coil power supply 337 are the same unit.

Adjacent to the imaging zone 338 is a radio frequency coil 340 for manipulating the orientations of magnetic spins within the imaging zone 338 and for receiving radio transmissions from spins also within the imaging zone 338. The radio frequency coil 340 is connected to a radio frequency transceiver 342. The radio frequency coil 340 and radio frequency transceiver 342 may be replaced by separate transmit and receive coils and a separate transmitter and receiver. It is understood that the radio frequency coil 340 and the radio frequency transceiver 342 are simply representative.

Within the center of the magnet is also located a subject 344. The subject 344 has a target zone 346 and is shown as reposing on a subject support 348.

The radio frequency transceiver 342, the magnetic field gradient coil power supply 336, the magnetic compensation coil power supply, the gantry 308, and the mechanical actuator 304are all shown as being connected to a hardware interface 354 of a computer system 352. The computer system 352 uses a processor 356 to control the therapeutic apparatus 300.

The computer system 352 shown in FIG. 3 is representative. Multiple processors and computer systems may be used to represent the functionality illustrated by this single computer system 352. The computer system 352 comprises the hardware interface 354 which allows the processor 356 to send and receive messages to components of the therapeutic apparatus 300. The processor 356 is also connected to a user interface 358, computer storage 360, and computer memory 362.

The computer storage 360 is shown as containing position data 370 that was measured by the position sensor 312. The computer storage 360 is further shown as containing field correction data 372. The computer storage is shown as further containing coil control commands 374 that are either a part of the field correction data 372 or were derived from the field correction data 372 using the position data 370 as a reference. The computer storage 360 is shown as further containing a pulse sequence 376. The pulse sequence as used herein encompasses a set of controls or commands which the magnetic resonance imaging system 306 may use to acquire magnetic resonance data. The computer storage 360 is shown as containing magnetic resonance data 378 which contains data acquired using the pulse sequence 376.

The computer memory 362 is shown as containing a control module 380. The control module 380 contains computer-executable code which enables the processor 356 to control the operation and function of the medical instrument 300. This may include such functions as using the pulse sequence 376 to acquire the magnetic resonance data 378. The control module 380 may also use the coil control commands 374 to control the power supplies 336 and/or 337 to compensate for inhomogeneities in the magnetic field within the imaging zone 338. The computer memory 362 is shown as further containing a coil control command generator module 382 which uses the position data 370 and the field correction data 372 to on the fly generate the coil control commands 374. In the different embodiments the coil control command generator module 382 may take different forms. For instance in one embodiment the coil control commands 374 are embedded or are contained in the field correction data 372 directly. In other embodiments the field correction data 372 contains a mapping of the inhomogeneities according to the position data 370. In this case the coil control command generator module 382 uses these recorded fields to then calculate what the coil control commands 374 should be.

In the embodiment shown in FIG. 3 the position data 370 may take different forms. In one embodiment position data simply contains the position of the gantry. In another embodiment the position data may also comprise the angular velocity of the gantry and also the prior position of the gantry. It should be noted that the angular velocity and the prior position may also be determined if the position is logged as a function of time. Depending upon the position data 370 the field correction data 372 may have different forms also. It may be simply a function of the absolute position of the gantry, or it may also contain a dependency upon the angular velocity and the prior position of the gantry.

Figure 4:
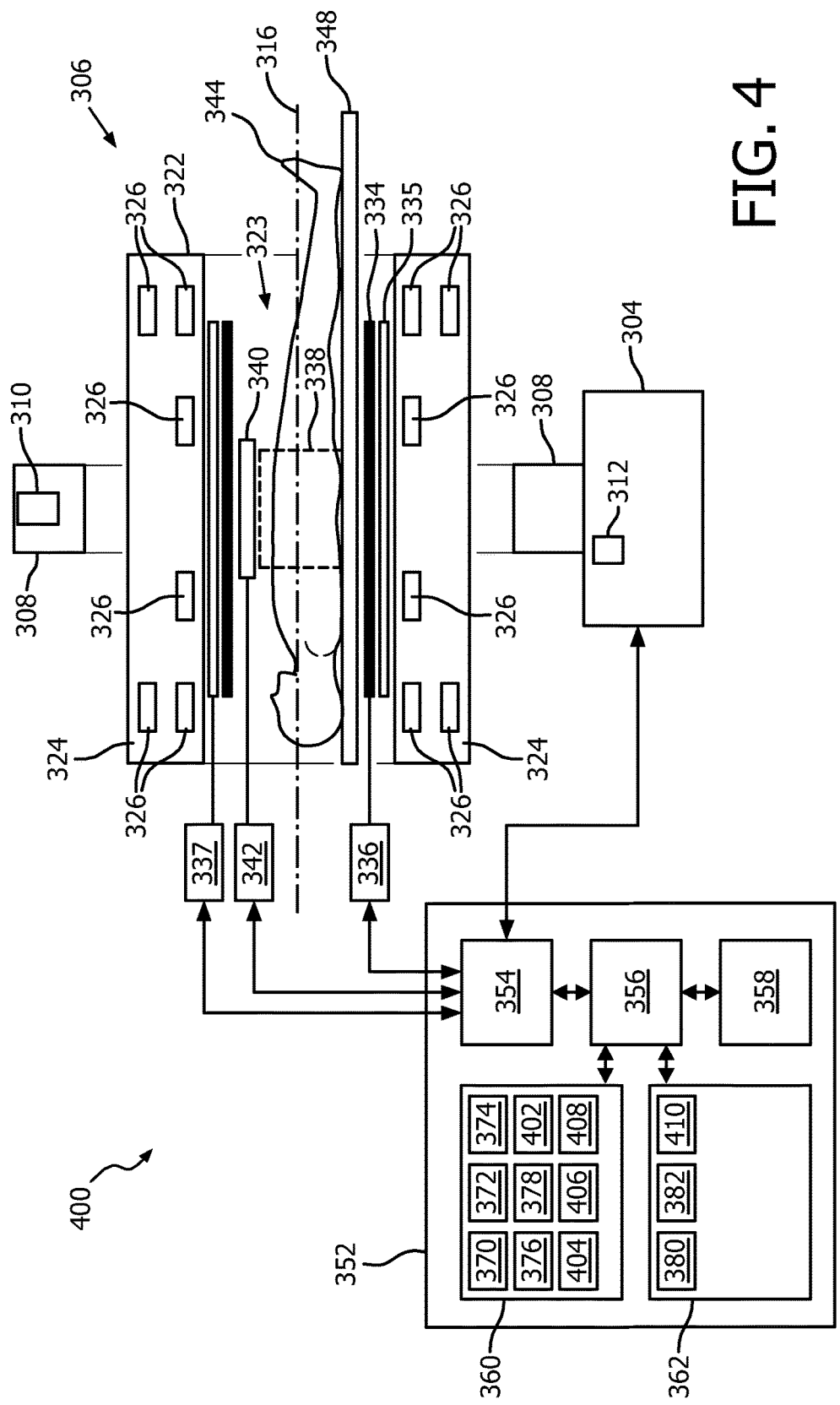
FIG. 4 illustrates a further example of a medical instrument.

FIG. 4 shows a further embodiment of a medical apparatus 400. The medical apparatus 400 is similar to the medical apparatus 300 shown in FIG. 3. There is additional software functionality shown in the medical apparatus 400.

The computer storage 360 is shown as containing a magnetic field measuring pulse sequence 402. The magnetic field measuring pulse sequence 402 contains control sequences which enable the magnetic resonance imaging system 306 to acquire magnetic field magnetic resonance data. The magnetic field magnetic resonance data is magnetic resonance data that comprises data which may be descriptive of the magnetic field within the imaging zone 338. The magnetic field measuring pulse sequence 402 may for instance be a pulse sequence as is described in the previously mentioned El-Sharkawy paper which is for instance is a gradient echo or a spoiled gradient echo experiment. Spectroscopic methods may also be used to measure the magnetic field.

The computer storage 360 is further shown as containing a magnetic field magnetic resonance data 403 acquired using the pulse sequence 402 and which is used to generate a magnetic field change map 404. The magnetic field change map 404 may be a map which indicates relative changes in the magnetic field and/or absolute values of the magnetic field within the imaging zone 338. The computer storage 360 is further shown as containing a magnetic resonance image 406 generated or reconstructed from the magnetic resonance data 378. The computer storage 360 is further shown as containing a phase corrected magnetic resonance image 408 that is the magnetic resonance image 406 which has had its phase corrected using the magnetic field change map 404.

The computer memory 362 is shown as containing an image reconstruction module 410. The image reconstruction module 410 contains computer-executable instructions which enables the processor 356 to generate the magnetic field change map 404 from the magnetic field magnetic resonance data 403, to generate the magnetic resonance image 406 from the magnetic resonance data 378, and to generate the phase corrected magnetic resonance image 408 using the magnetic resonance image 406 and the magnetic field change map 404.

Figure 5:
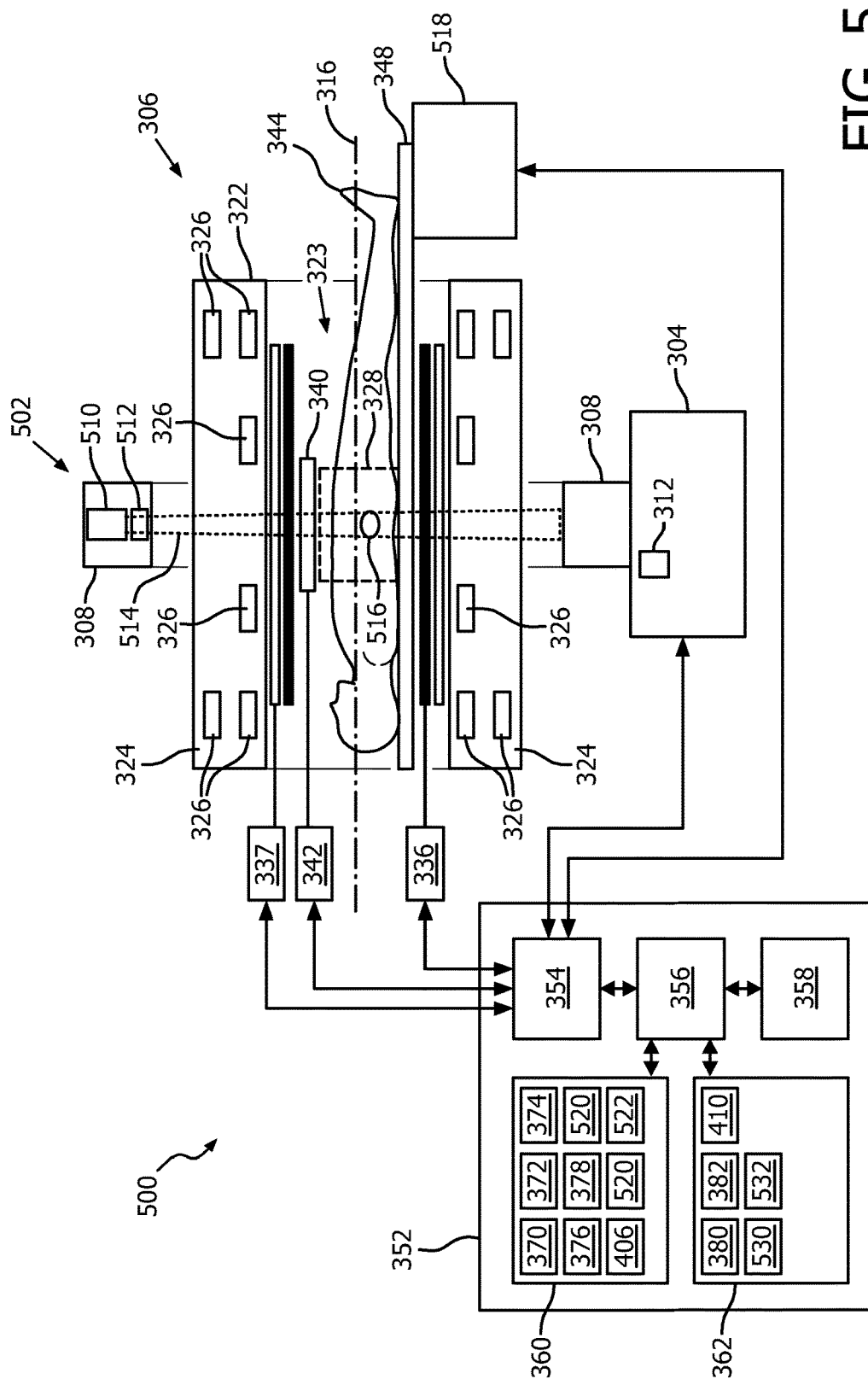
FIG. 5 illustrates a further example of a medical instrument.

FIG. 5 shows a medical apparatus 500 that is similar to the medical apparatuses shown in FIGS. 3 and 4. It should be noted that the features of the different medical apparatuses shown in FIGS. 3, 4, and 5 may be combined.

The medical apparatus 500 shown in FIG. 5 is similar to that shown in FIGS. 3 and 4 except that a radiotherapy device 502 has been added to the gantry 308. The radiotherapy device 502 is intended to be representative of nearly any type of radiotherapy device which may be mounted onto a gantry 308. The radiotherapy device may for instance, but is not limited to: a Linac, a charged particle source and an X-ray source. In this example the radiotherapy device 502 comprises a radiotherapy source 510 and a beam collimator 512. Both the radiotherapy source 510 and/or the beam collimator 512 may be a magnetic field distorting component. The radiotherapy source 510 generates a radiation beam 514 which is shown as going through the cryostat 324. Other arrangements may also be used for example a split magnet or an open magnet may also be used. The gantry 308 revolves around the axis 316 and as this happens a target zone 516 within the subject 344 is able to be irradiated by the radiotherapy source 510. Also shown is a mechanical positioning system 518 for positioning the subject support 348. The radiotherapy device 502 and the subject support 518 are both controlled by the hardware interface 354.

In this embodiment the computer storage 360 is shown as additionally containing a treatment plan 520 and radiotherapy control signals 522. The radiotherapy control signals 522 are generated by a radiotherapy apparatus control module using the treatment plan 520 and the magnetic resonance image 406. The treatment plan 520 contains instructions for irradiating the target zone 516 and then the magnetic resonance image 406 is used to register or control the actual functioning of the radiotherapy device 502 in a real time basis to account for motion of the subject and/or changes in the internal anatomy. The computer memory 362 is further shown as containing a mechanical actuator control module 532 which enables the processor 356 to control the mechanical positioning system 518.

The integration of a Magnetic Resonance (MR) and a Linac system poses high requirements concerning minimal mutual electro-magnetic system interference. For instance, magnetic material in the Linac-Gantry which is not distributed uniformly over its circumference can distort the magnetic field of the MR system, which leads to imaging artifacts. Means for correcting these distortions and other artifacts using a combination of gantry position sensors, pre-calibrated look-up tables, and/or active field distortion correction coils and signal phase correction schemes may be used.

The Linac gantry contains magnetic material which is not distributed uniformly over its circumference. This material is magnetized by the residual stray field of the magnet (which has rotational symmetry) and by secondary fields from the environment (including the geomagnetic field).

The magnetization of all these parts causes an inhomogeneous additional field in the imaging volume of the scanner, which to first approximation rotates with the Linac gantry but which may also subtly change shape during rotation. In order to obtain good quality images while the Linac rotates, the variations of this gantry-related field should remain smaller than 50 nano Tesla for all volume elements of the imaging volume. It can be assumed that the gantry fields are reduced to approximately 1 micro Tesla or less by adding magnetic material to the gantry.

Magnetic material in the Linac-Gantry which is not distributed uniformly over its circumference can distort the magnetic field of the MR system, which leads to imaging artifacts.

One possible solution employs several components/steps:
  gantry position sensor: to determine the exact rotational angle of the Linac gantry,
  recording and storage of a look-up-table which relates gantry position and generated field-distortion ("pre-calibration"),
  method and device to control the current through compensation coils which compensate (most of) the field distortion
  method to compensate for remaining error via phase correction in the recorded imaging data.

In a pre-calibration phase the rotation-dependent gantry field is measured using NMR magnetometry for a large number of gantry angles. These field maps are decomposed into a suitable set of parameters such as the coefficients of a spherical harmonic expansion, which allow accurate reconstruction of the corresponding field pattern.

These field coefficients are stored in the scanner computer in a lookup table. The output of a position sensor of the Linac gantry is transmitted to the scanner computer so that for each position of the gantry the computer can evaluate an appropriate set of error field coefficients (by interpolation between the nearest look up table values). This set of error coefficients may then used to determine a set of currents in compensation coils, so as to largely compensate for the unwanted field.

Instead of storing the position dependent field map data, it is also possible to store the pre-computed values of the currents in the correction coils needed to compensate for the position-dependent field errors.

The correction of linear gradient fields can be accomplished by adding suitable offsets to the DC current flowing in the x, y and z gradient coils. Higher order correction fields require additional dedicated higher order correction coils. A uniform error field component can be generated by a uniform field correction coil or its effect can be compensated by adjustment of the operating frequency of the system.

As preliminary measurements indicate a certain rpm-dependency, measures for moving gantry treatment regimes have to be considered too. Therefore the gantry speed can be taken into account as an additional parameter.

Still remaining field errors after this active correction can be predicted from the known (dynamic) error field to be corrected and the known fields generated by the active correction measures implemented on the system. These residual field errors can be used for a phase correction in the acquired data so as to further minimize the artifacts arising from the field errors.

Figure 6:
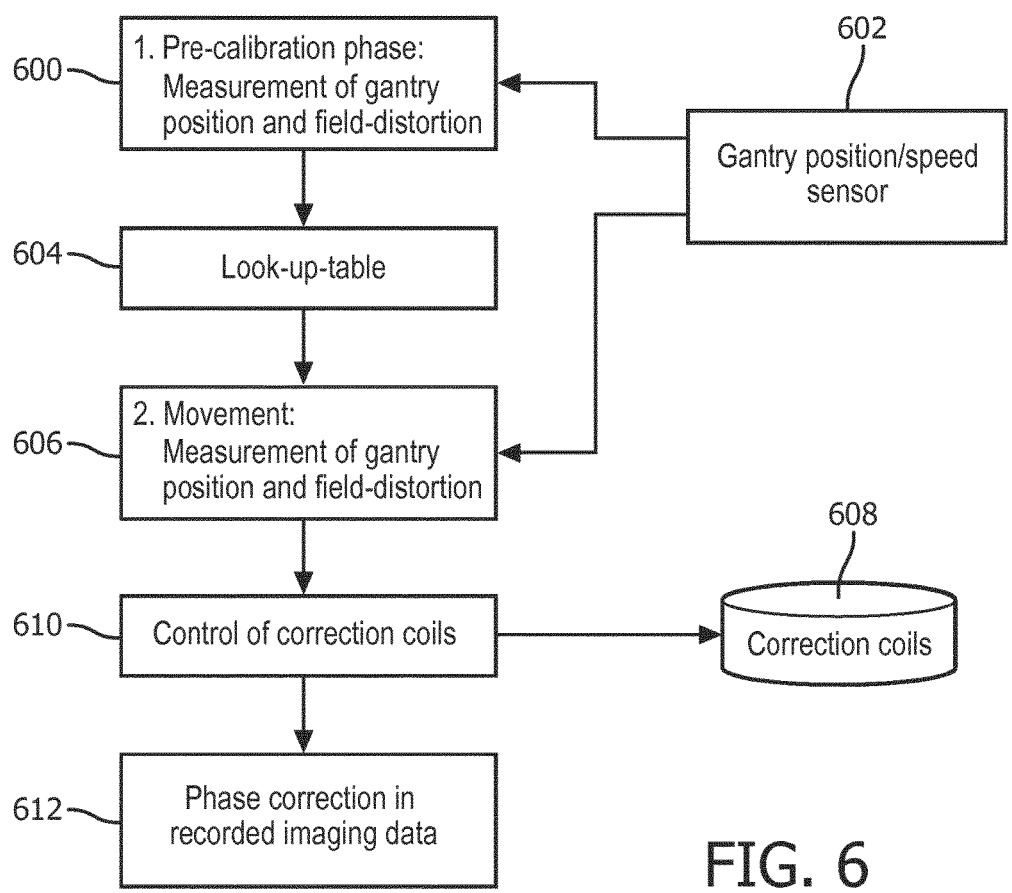
FIG. 6 shows a flow diagram which illustrates a further example of a method.

FIG. 6 shows a flow diagram which illustrates an example of a method. First in step 600 a pre-calibration phase is performed. In this phase the measurement of the gantry position and any field distortions caused by the position of the gantry is measured. This is referenced to the gantry position and/or speed 602. The data from step 600 is then used to construct a lookup table 604 which references the gantry position, speed, and/or prior position to the field measurements. The lookup table 604 may have simply a recall of the measured field values or it may also contain controls for controlling the correction coils. Next in step 606 a movement phase is performed. In this case the measurements are performed using the magnetic resonance imaging system as the gantry is moved. The position sensor 602 provides position and/or speed data on the position of the gantry and then the lookup table 604 is used to drive control commands for the corrections of the coil 610. These control commands 610 are then sent to the correction coil 608. In step 612 is an optional step where a phase correction is performed in the recorded magnetic resonance image data.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 300 therapeutic apparatus
304 mechanical actuator
306 magnetic resonance imaging system
308 gantry
310 magnetic field distorting component
312 position sensor
316 rotational axis
322 magnet
323 bore of magnet
324 cryostat
326 superconducting coil
334 magnetic field gradient coil
335 magnetic compensation coil
336 magnetic field gradient coil power supply
337 magnetic compensation coil power supply
338 imaging zone
340 radio frequency coil
342 radio frequency transceiver 344 subject
348 subject support
352 computer system
354 hardware interface
356 processor
358 user interface
360 computer storage
362 computer memory
370 position data
372 field correction data
374 coil control commands
376 pulse sequence
378 magnetic resonance data
380 control module
382 coil control command generator module
400 medical apparatus
402 magnetic field measuring pulse sequence
403 magnetic field magnetic resonance data
404 magnetic field change map
406 magnetic resonance image
408 phase corrected magnetic resonance image
410 image reconstruction module
500 medical apparatus
502 radio therapy device
510 radio therapy source
512 beam collimator
514 radiation beam
516 target zone
518 mechanical positioning system
520 treatment plan
522 radio therapy control signals
530 radio therapy apparatus control module
532 mechanical actuator control module

The invention claimed is:

1. A medical apparatus comprising:
a magnetic resonance imaging system for acquiring magnetic resonance data from an imaging zone, wherein the magnetic resonance imaging system comprises a magnet for generating a magnetic field within the imaging zone;
magnetic compensation coils for compensating for magnetic inhomogeneities in the magnetic field within the imaging zone;
a gantry operable for rotating about the imaging zone, wherein the gantry is configured to rotate about a rotational axis;
a position sensor for measuring position data, the position data comprising an angular position of the gantry and an angular velocity of the gantry;
at least one magnetic field distorting component, wherein the gantry is further operable to rotate the at least one magnetic field distorting component about the rotational axis;
a memory for storing machine executable instructions and field correction data, wherein the field correction data is descriptive of the magnetic field within the imaging zone as a function of the angular position and the angular velocity;
a processor for controlling the medical apparatus, wherein execution of the instructions cause the processor to:
receive the position data from the position sensor;
determine coil control commands for controlling the magnetic compensation coils using the field correction data and the position data;
control the magnetic compensation coils to compensate for magnetic inhomogeneities within the imaging zone caused by the at least one magnetic field distorting component using the coil control commands; and
acquire the magnetic resonance data using the magnetic resonance imaging system.

2. The medical apparatus of claim 1, wherein the field correction data is further descriptive of the magnetic field within the imaging zone as a function of prior angular positions and/or configurations of the gantry, wherein execution of the instructions further causes the processor to:
log the position data in a position database; and
determine prior angular positions of the gantry from the position database, wherein the coil control commands are determined using at least the field correction data, the position data, and the prior angular positions.

3. The medical apparatus of claim 1, wherein the field correction data comprises pre-calculated coil control commands.

4. The medical apparatus of claim 1, wherein the field correction data comprises spatially dependent magnetic field measurements within the imaging zone, and wherein the coil control commands are determined using a magnetic field model of the magnetic compensation coils to compensate for spatially dependent magnetic field measurements.

5. The medical apparatus of claim 1, wherein execution of the instructions further causes the processor to:
measure magnetic field magnetic resonance data using the magnetic resonance imaging system before measuring the magnetic resonance data, and
determine a magnetic field change within the imaging zone.

6. The medical apparatus of claim 5, wherein execution of the instructions further causes the processor to:
calculate a phase offset using the magnetic field change, and
correct the magnetic resonance data using the phase offset.

7. The medical apparatus of claim 5, wherein execution of the instructions further causes the processor to:
modify the coil control commands to compensate for the magnetic field change.

8. The medical apparatus of claim 1, wherein the medical device comprises a radiotherapy device, wherein the radiotherapy device comprises the at least one magnetic field distorting component.

9. The medical apparatus of claim 8, wherein the radiotherapy device is selected from the group consisting of a LINAC, a charged particle source, and an X-ray source and/or wherein the at least one magnetic field distorting component comprises at least one of: a magnetic field source, an coil, a solenoid, charged particle optics, a magnet, an electromagnet, a permanent magnet, a ferromagnetic component, a ferrimagnetic component, a paramagnetic component, a diamagnetic component, a magnetic component, and combinations thereof.

10. A method of controlling a medical apparatus,
wherein the medical apparatus comprises a magnetic resonance imaging system arranged to acquire a magnetic resonance data from an imaging zone,
wherein the magnetic resonance imaging system comprises a magnet for generating a magnetic field within the imaging zone,
wherein the medical apparatus comprises magnetic compensation coils for compensating for magnetic inhomogeneities in the magnetic field within the imaging zone, wherein the medical apparatus further comprises a gantry operable for rotating about the imaging zone,
wherein the gantry is configured to rotate about a rotational axis,
wherein the medical apparatus further comprises a position sensor for measuring position data, the position data comprising an angular position of the gantry and an angular velocity of the gantry,
wherein the medical apparatus further comprises at least one magnetic field distorting component,
wherein the gantry is further operable to rotate the at least one magnetic distorting component about the rotational axis,
the method comprising the steps of:
receiving the position and velocity data from the position sensor;
determining coil control commands for controlling the magnetic compensation coils using the field correction data and the position and velocity data, wherein the field correction data is descriptive of the magnetic field within the imaging zone as a function of the angular position and the angular velocity;
controlling the magnetic compensation coils to compensate for magnetic inhomogeneities within the imaging zone caused by the at least one magnetic field distorting component using the coil control commands; and
acquiring the magnetic resonance data using the magnetic resonance imaging system.

11. The method of claim 10, wherein the field correction data is further descriptive of the magnetic field within the imaging zone as a function of prior angular positions of the gantry, wherein the method further comprises the steps of:
logging the position data in a position database; and
determining prior angular positions of the gantry from the position database, wherein the coil control commands are determined using at least the field correction data, the position data, and the prior angular positions.

12. The method of claim 10, wherein the method further comprises the steps of:
measuring magnetic field measurements in the imaging zone, wherein the magnetic field is measured using any one of the following: a magnetometer, a magnetic resonance protocol to control the magnetic resonance imaging system, and combinations thereof; and
determining the field correction data using the magnetic field measurements.

13. A non-transitory computer-readable medium containing computer executable instructions operable for causing a computer to perform a method of controlling a medical apparatus,
wherein the medical apparatus comprises a magnetic resonance imaging system arranged to acquire a magnetic resonance data from an imaging zone,
wherein the magnetic resonance imaging system comprises a magnet for generating a magnetic field within the imaging zone,
wherein the medical apparatus comprises magnetic compensation coils for compensating for magnetic inhomogeneities in the magnetic field within the imaging zone,
wherein the medical apparatus further comprises a gantry operable for rotating about the imaging zone,
wherein the gantry is configured to rotate about a rotational axis,
wherein the medical apparatus further comprises a position sensor for measuring position data, the position data comprising an angular position of the gantry and an angular velocity of the gantry,
wherein the medical apparatus further comprises at least one magnetic field distorting component,
wherein the gantry is further operable to rotate the at least one magnetic distorting component about the rotational axis,
the method comprising the steps of:
receiving the position and velocity data from the position sensor;
determining coil control commands for controlling the magnetic compensation coils using the field correction data and the position and velocity data, wherein the field correction data is descriptive of the magnetic field within the imaging zone as a function of the angular position and the angular velocity;
controlling the magnetic compensation coils to compensate for magnetic inhomogeneities within the imaging zone caused by the at least one magnetic field distorting component using the coil control commands; and
acquiring the magnetic resonance data using the magnetic resonance imaging system.

14. A medical apparatus comprising:
a magnetic resonance imaging system configured to acquire magnetic resonance data from an imaging zone, the magnetic resonance imaging system including a magnet configured to generate a magnetic field within the imaging zone;
at least one magnetic field distorting structure configured to rotate around the imaging zone;
a sensor configured to measure (i) angular position data indicative of an angular position of the at least one magnetic field distorting structure around the imaging zone, and (ii) angular velocity data indicative of an angular velocity of the at least one magnetic field distorting structure around the imaging zone;
magnetic field inhomogeneity compensation coils configured to be controlled to compensate for magnetic field inhomogeneities in the magnetic field within the imaging zone, the magnetic field inhomogeneities being caused by the rotating magnetic field distorting structure;
a memory configured to store the magnetic field correction data, the magnetic field correction data being descriptive of at least one of magnetic field and magnetic field inhomogeneities within the imaging zone as a function of both the angular position and the angular velocity of the magnetic field distorting structure;
a computer processor configured to:
receive the angular position data and the angular velocity data from the sensor,
control the magnetic field compensation coils to compensate for magnetic field inhomogeneities in the imaging zone using the magnetic field correction data, the received angular position data, and the received angular velocity data, and
acquire magnetic resonance data from the magnetic field inhomogeneity corrected imaging zone of the magnetic resonance imaging system.

15. The medical apparatus of claim 14, wherein the magnetic field compensation coils include gradient magnetic field coils of the magnetic resonance imaging system and additional magnetic field coils configured to compensate for higher order corrections than the gradient coils.

16. The medical apparatus of claim 14, further including an additional ferromagnetic object stationarily disposed adjacent the imaging zone which induces additional magnetic field distortions in the magnetic field in addition to the angular position and angular velocity dependent distortions in the magnetic field induced by the rotating at least one magnetic field distorting structure.

17. The medical apparatus of claim 14, wherein the computer processor is further configured to:
   determine a magnetic field change in the imaging zone;
   calculate a phase offset using the magnetic field change; and
   correct the acquired magnetic resonance data using the phase offset.

18. The medical apparatus of claim 17, wherein the computer processor is further configured to:
   modify the control of the magnetic field compensation coils to compensate for the magnetic field change.

19. The medical apparatus of claim 14, wherein the at least one magnetic field distorting structure includes at least one of a linear accelerator (LINAC), a charged particle source, and an x-ray source.

20. The medical apparatus of claim 14, wherein the at least one magnetic field distorting structure includes one of a magnetic field source, a coil, a solenoid, charged particle optics, a magnet, an electromagnet, a permanent magnet, a ferromagnetic structure, a ferrimagnetic structure, a paramagnetic structure, a diamagnetic structure, and a magnetic structure.

* * * * *